United States Patent
Corbeil (10) Patent No.: US 10,912,528 B2
(45) Date of Patent: Feb. 9, 2021

(54) IN-LINE PET DETECTOR CONFIGURATION FOR A COMBINED PET AND CT IMAGING SYSTEM

(71) Applicant: Siemens Medical Solutions USA, Inc., Malvern, PA (US)

(72) Inventor: James L. Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1306 days.

(21) Appl. No.: 14/480,904

(22) Filed: Sep. 9, 2014

(65) Prior Publication Data

US 2015/0073272 A1 Mar. 12, 2015

Related U.S. Application Data

(60) Provisional application No. 61/876,828, filed on Sep. 12, 2013.

(51) Int. Cl.
*A61B 6/00* (2006.01)
*A61B 6/03* (2006.01)
*A61B 6/04* (2006.01)

(52) U.S. Cl.
CPC ............ *A61B 6/4417* (2013.01); *A61B 6/032* (2013.01); *A61B 6/037* (2013.01); *A61B 6/0487* (2020.08); *A61B 6/42* (2013.01)

(58) Field of Classification Search
None
See application file for complete search history.

(56) References Cited

U.S. PATENT DOCUMENTS

| | | | |
|---|---|---|---|
| 8,001,643 B1* | 8/2011 | James | F16L 3/23 |
| | | | 14/69.5 |
| 2003/0058984 A1* | 3/2003 | Susami | A61B 6/4417 |
| | | | 378/19 |
| 2005/0067577 A1* | 3/2005 | Yanagita | G01T 1/2928 |
| | | | 250/370.09 |
| 2005/0067578 A1* | 3/2005 | Ueno | A61B 6/032 |
| | | | 250/370.09 |
| 2006/0018437 A1* | 1/2006 | Russinger | A61B 6/035 |
| | | | 378/197 |
| 2009/0159804 A1* | 6/2009 | Shibuya | G01T 1/2985 |
| | | | 250/363.03 |

FOREIGN PATENT DOCUMENTS

JP  2010005472 A  * 1/2010

* cited by examiner

*Primary Examiner* — Pascal M Bui Pho
*Assistant Examiner* — Marjan Saboktakin (57) ABSTRACT

A positron emission tomography (PET) detector configuration for a combined PET and computed tomography (CT) imaging system, wherein the CT system includes an annular cavity. The configuration includes a backplane having a neutral axis and an aperture. In addition, the configuration includes at least one PET detector located about the aperture, wherein a center of mass of the at least one PET detector is in-line with the neutral axis and wherein a portion of the at least one PET detector is located in the annular cavity thereby reducing a footprint of the combined PET and CT imaging system. Further, the location of the at least one PET detector reduces the strength needed for maintaining structural integrity of the backplane.

18 Claims, 7 Drawing Sheets

IN-LINE PET DETECTOR CONFIGURATION FOR A COMBINED PET AND CT IMAGING SYSTEM

CROSS REFERENCE TO RELATED APPLICATION

This application claims the benefit under 35 U.S.C. § 119(e) of U.S. Provisional Application No. 61/876,828 entitled A BALANCED APPROACH, THE DEPLOYMENT OF PET DETECTORS ON AN OPTIMIZED GANTRY, filed on Sep. 12, 2013 which is incorporated herein by reference in its entirety and to which this application claims the benefit of priority.

FIELD OF THE INVENTION

The invention relates to combined positron emission tomography (PET) and computed tomography (CT) imaging systems and more particularly, to a PET detector configuration wherein at least one PET detector is located in-line with a neutral axis of a backplane to reduce an amount of stress on the backplane.

BACKGROUND OF THE INVENTION

In medical imaging, a computed tomography (CT) scanning technique may be used to provide images of the internal structures of a human body, such as the bones. In addition, a positron emission tomography (PET) scanning technique may be used to provide images of the functional aspects of the body, usually corresponding to the metabolic uptake of an internal organ or tissue. It is frequently desirable to combine the CT and PET scanning techniques to provide a co-registered image or series of images to assist in non-invasively study physiological processes and structures within the body.

In a CT scan, an x-ray source is passed around a patient. Detectors around the patient then respond to an x-ray transmission through the patient to produce an image of the area of study. In a PET scan, a short-lived radioisotope is injected into a patient. For example, one such radioisotope is fluorodeoxyglucose (FDG). During the PET scan, the patient is positioned in a tunnel within a gantry. The radioisotope undergoes positron emission decay and emits a positron, which is the antimatter counterpart of an electron. The positron encounters and annihilates with an electron to produce a pair of gamma rays moving in approximately opposite directions. The gamma rays are then detected by a plurality of PET detectors arranged around a circumference of the tunnel.

Figure 1:
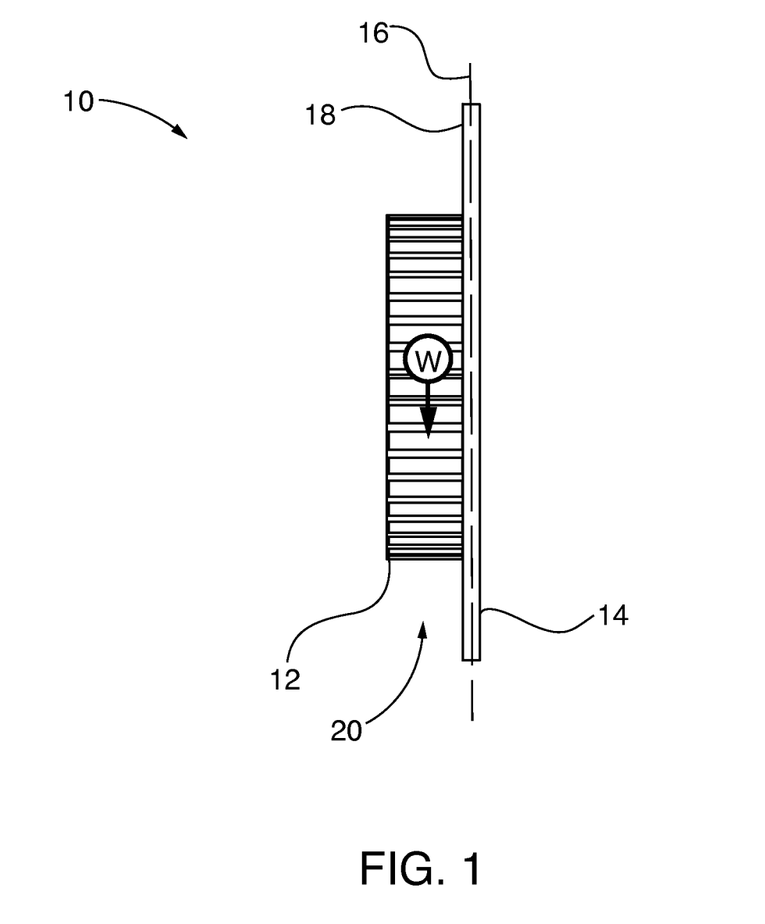
FIG. 1 depicts a conventional configuration for cantilevered PET detectors arranged on gantry backplane.

Referring to FIG. 1, a configuration 10 for cantilevered PET detectors 12 arranged on gantry backplane 14 is shown. The backplane 14 has a neutral or vertical axis 16. The cantilevered PET detectors 12 are configured such that they extend from a face 18 of the backplane to form a cantilevered PET detector arrangement 20. The center of mass of the cantilevered PET detectors 12 does not fall on the neutral axis 16 of the backplane 14. The cantilevered detector arrangement 20 requires a very rigid structure in order to support a moment load W generated by the cantilevered PET detectors 12. Further, the cantilevered detector arrangement 20 magnifies the vibrational energy generated by a PET system thus undesirably subjecting the cantilevered PET detectors 12 to the magnified vibrational energy.

SUMMARY OF INVENTION

A positron emission tomography (PET) detector configuration for a combined PET and computed tomography (CT) imaging system is disclosed wherein the CT system includes an annular cavity. The configuration includes a PET backplane having a neutral axis and an aperture. In addition, the configuration includes at least one PET detector located about the aperture, wherein a center of mass of the at least one PET detector is in-line with the neutral axis and wherein a portion of the at least one PET detector is located partially within the annular cavity thereby reducing a footprint of the combined PET and CT imaging system. Further, the location of the at least one PET detector reduces a strength needed for maintaining structural integrity of the backplane.

The respective features of the present invention may be applied jointly or severally in any combination or sub-combination by those skilled in the art.

BRIEF DESCRIPTION OF DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 2A:
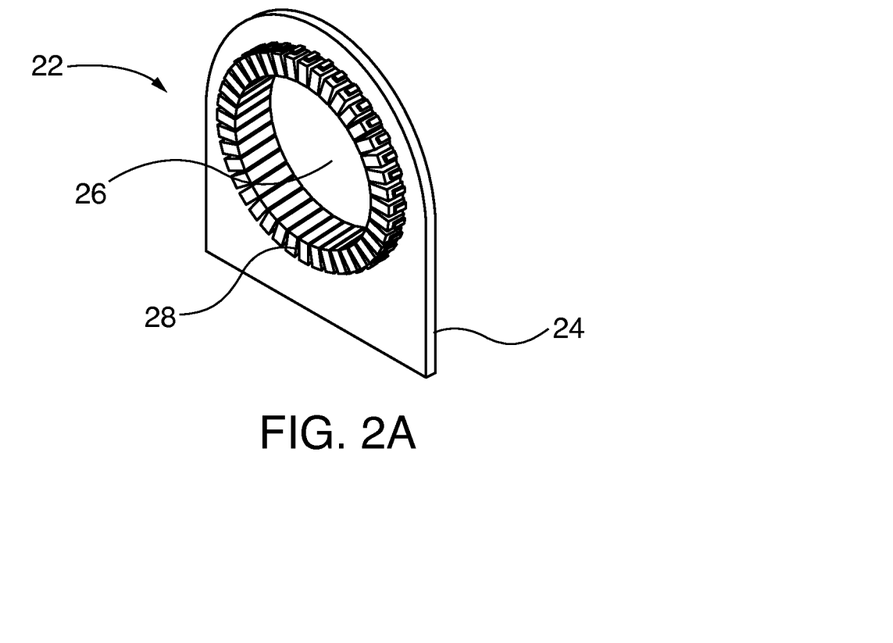
FIGS. 2A and 2B show an in-line PET detector configuration for a PET scanning system in accordance with the invention.
Figure 2B:
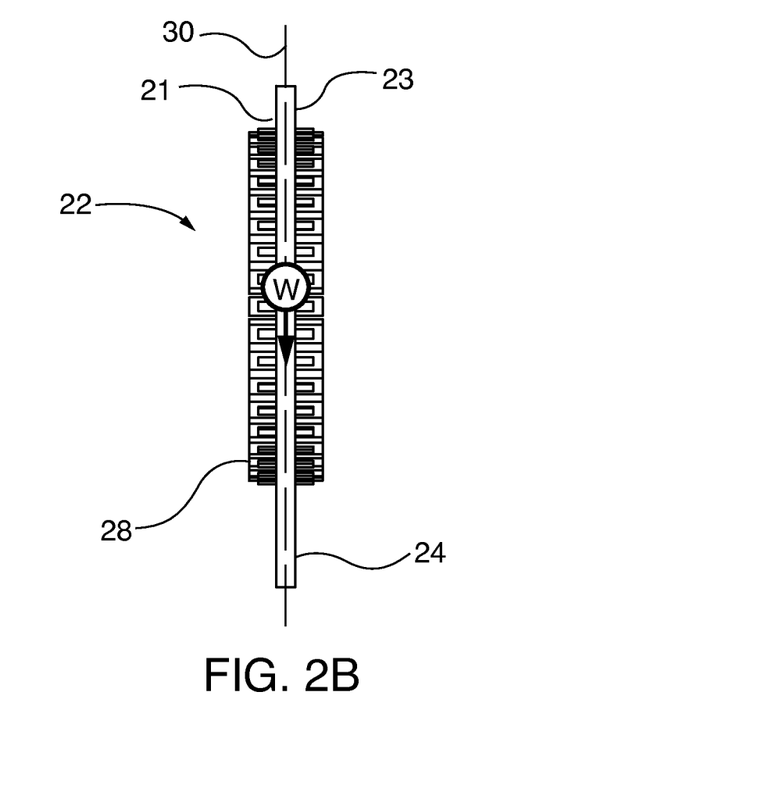

Referring to FIGS. 2A and 2B, an in-line PET detector configuration 22 for a PET scanning system in accordance with the invention is shown. The in-line configuration 22 includes a gantry backplane 24 having a circular aperture 26 that forms part of a tunnel as will be described. At least one PET detector 28, or a plurality of PET detectors 28, is circumferentially arranged on the backplane 24 about the aperture 26. A center of mass of each PET detector 28 is positioned in-line with a neutral or vertical axis 30 (i.e. in-line PET detectors 28) of the backplane 24. Positioning the center of mass of each PET detector 28 in-line with the vertical axis 30 of the backplane 24 eliminates a moment load caused by the cantilevered PET detectors 12. As a result, stresses on the backplane 24 are reduced, thus enabling the use of a backplane 24 requiring less strength for maintaining structural integrity. This provides additional design flexibility and material choices for fabricating the backplane 24. For example, the backplane 24 may be fabricated from relatively inexpensive foam or cardboard material sandwiched between sheets of aluminum, thus reducing fabrication costs. In addition, the current invention enables fabrication of a lighter backplane 24 resulting in reduced transportation and installation costs. Further, the in-line PET detectors 28 are not subjected to magnified vibrational energy. As can be seen from FIG. 2B, the in-line PET detectors 28 extend from first 21 and second 23 faces of the backplane 24.

Figure 3A:
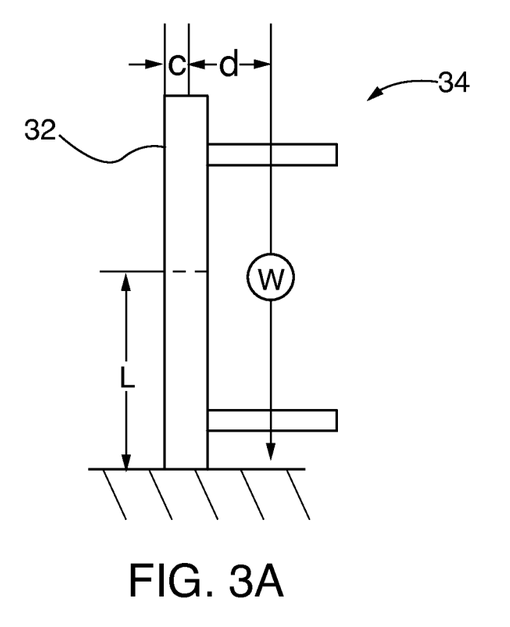
FIGS. 3A-3B show top and side views, respectively, of an exemplary cantilevered detector arrangement used to calculate stress in conjunction with Table 1.
Figure 3B:
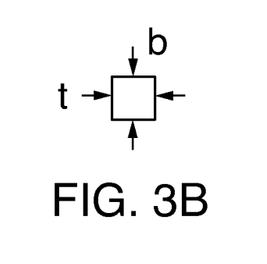
Figure 4A:
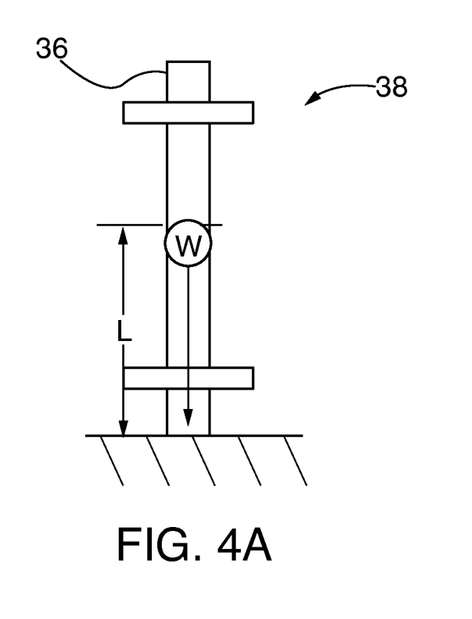
FIGS. 4A-4B show top and side views, respectively, of an exemplary in-line detector configuration used to calculate stress in conjunction with Table 1.
Figure 4B:
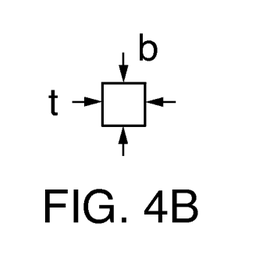

Referring to FIGS. 3A-4B in conjunction with Table 1, exemplary calculations are shown for stress exerted on a backplane 32 for an exemplary cantilevered detector arrangement 34 (see FIGS. 3A-3B) and a backplane 36 an exemplary in-line detector configuration 38 (See FIGS. 4A-4B) in accordance with the invention. For purposes of clarity, only two detectors are shown in FIGS. 3A and 4A. Further, FIGS. 3B and 4B are top views of the backplanes 32 and 36, respectively. It is noted that the dimensions set forth in TABLE 1 are for illustrative purposes only.

TABLE 1

| Constant | Value | Units | Equation |
| --- | --- | --- | --- |
| Gantry Width, b | 1.5 | m | |
| Height (CM), L | 1.12 | m | |
| Moment Arm, d | 0.128 | m | |
| Gantry Thickness, t | 0.05 | m | |
| Effective Detector Mass, m | 160 | kg | |
| Gravitational Acceleration, g | 9.81 | m/s$^2$ | |
| Distance to neutral axis, c | 0.025 | m | t/2 |
| Area, A | 0.075 | m$^2$ | t × b |
| Weight, W | 1569.60 | N | m × g |
| Moment, M | 200.909 | Nm | N × d |
| Moment of Inertia, I | 0.000015625 | m$^4$ | (b × t$^3$)/12 |

TABLE 1-continued

| Constant | Value | Units | Equation |
| --- | --- | --- | --- |
| Bending Stress, S$_b$ Cantilevered Detectors | 321.454 | kPa | (M × c)/I |
| Axial Stress, S$_a$ In-line Detectors | 20.928 | kPa | W/A |

Thus, the amount of stress $S_b$ on the backplane 32 having the cantilevered detector arrangement 34 is approximately 15 times greater than the amount of amount of stress $S_a$ on the backplane 36 having the in-line detector configuration 38 (i.e. 321.454/20.928=15.36). Therefore, the strength of the backplane 38 having the in-line detector configuration 38 may be reduced by factor of approximately 15 as compared to the strength needed for the cantilevered detector arrangement 34.

Figure 5:
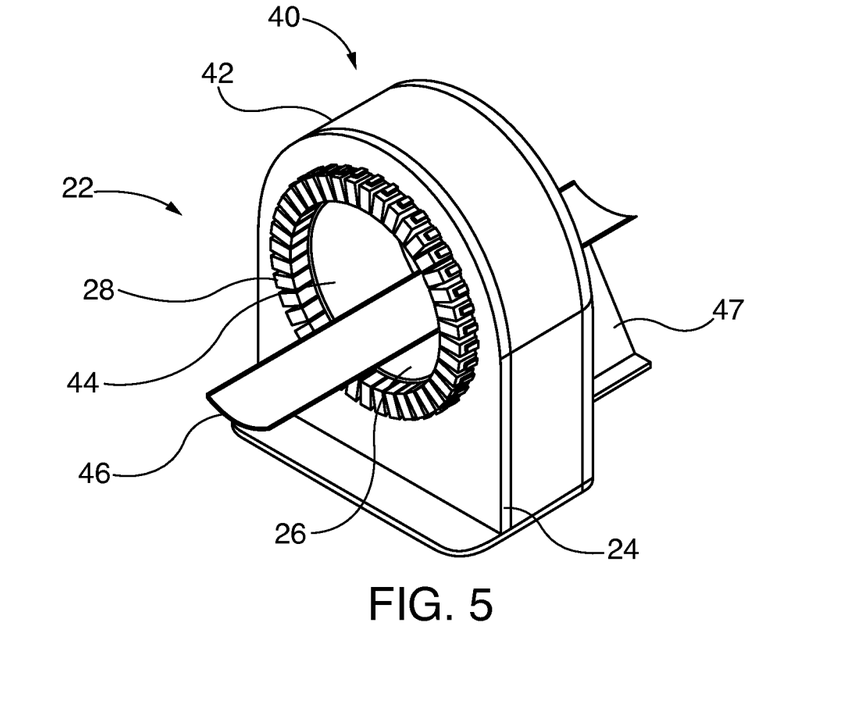
FIG. 5 is a partial view of a PET and CT imaging system which depicts a backplane including in-line PET detectors arranged in an in-line PET detector configuration.

Referring to FIG. 5, a partial view of a PET and CT imaging system 40 is shown which depicts the backplane 24 including the in-line PET detectors 28 arranged in the in-line PET detector configuration 22. The combined system 40 includes an enclosure 42 having a tunnel 44 that includes a bed 46 for holding a patient. The bed 46 is supported by a bed traversing mechanism 47 that serves to move the bed 46 and thus patient relative to the tunnel 44 during scanning. Alternatively, the bed 46 is stationary and the combined system 40 moves relative to the bed 46. The aperture 26 (see FIG. 2A) forms part of the tunnel 44. During scanning, the bed 46 is moved within the tunnel 44. The combined system 40 utilizes known PET and CT scanning techniques and associated components to generate PET and CT scans of the patient either sequentially or simultaneously without requiring the patient to get off the bed 46. With regard to combined PET and CT imaging systems, the entire disclosure of U.S. Pat. No. 6,449,331, issued on Sep. 10, 2002, and entitled COMBINED PET AND CT DETECTOR AND METHOD FOR USING SAME, is hereby incorporated by reference in its entirety.

The in-line PET detectors 28 may be of the type known as time-of-flight (TOF) detectors. A TOF detector has enhanced sensitivity due to the better positioning (through better electronic timing) of events along a line of coincidence. Alternatively, non-TOF types of detectors may be used. Further, in-line PET detectors 28 may include photo sensors such as photomultiplier tubes (PMTs), avalanche photo diodes (APDs) and/or silicon photo multipliers (SiPMs). It is understood that other types of detectors may be used.

Figure 6:
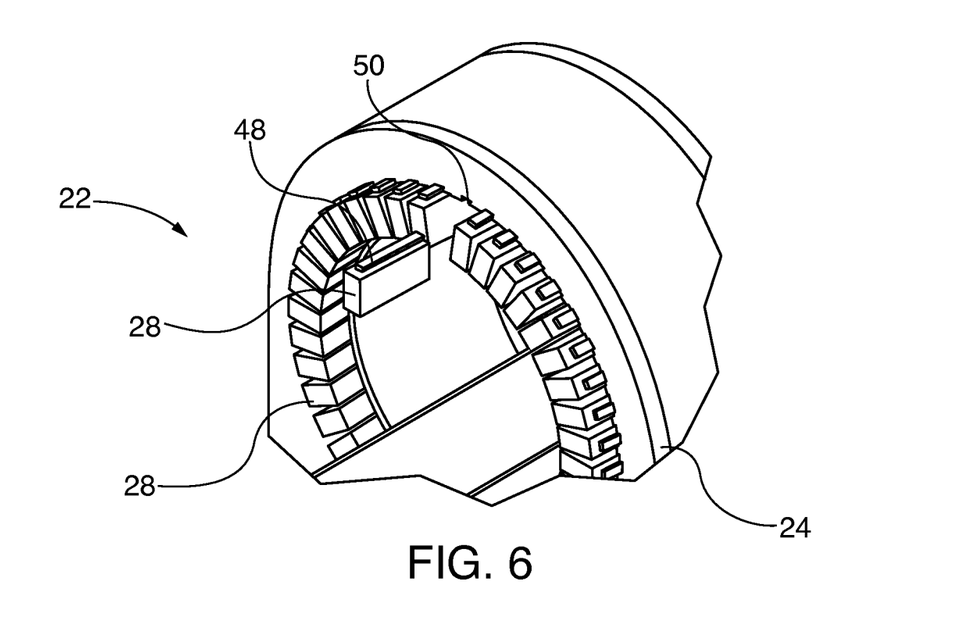
FIG. 6 is a view of a PET detector prior to insertion into a backplane in accordance with the invention.
Figure 7A:
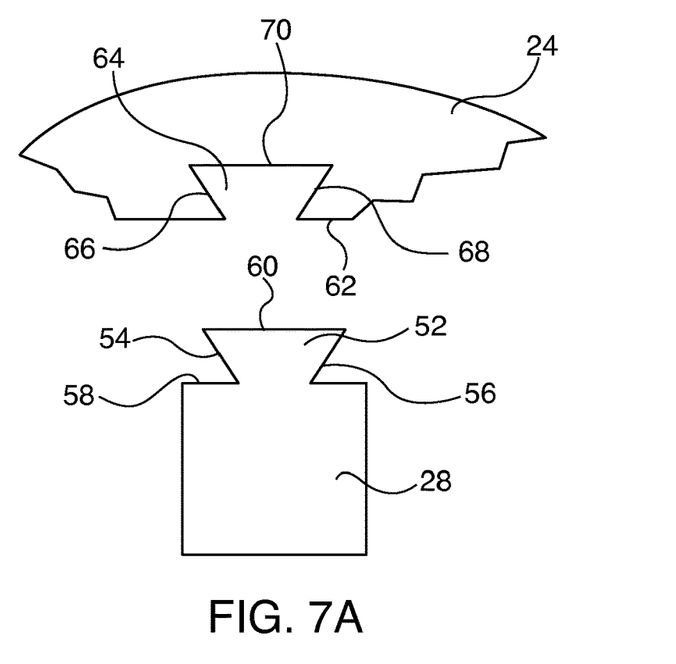
FIG. 7A is an end view of an exemplary PET detector having an attachment portion in accordance with the invention.

The length of an in-line PET detector 28 may vary depending on the detector type. In particular, the length determines an imaging field of view (FOV). Referring to FIG. 6, a view of a PET detector 28 prior to insertion into the backplane 24 is shown. Each PET detector 28 includes an attachment portion 48 that is inserted into a corresponding hole 50 in the backplane 24. Referring to FIG. 7A, an end view of an exemplary PET detector 28 is shown. In an embodiment, an attachment portion 52 includes angled sidewalls 54,56 that extend outwardly from an upper portion 58 of the PET detector 28. A horizontal top wall 60 extends between the sidewalls 54,56 to form an attachment portion 52 having a substantially dovetail shape. The attachment portion 52 extends along a length of the PET detector 28. An inner circumference 62 of the backplane 24 includes a hole 64 defined by a horizontal wall 70 located between sidewalls 66,68 to form a corresponding dovetail shape for receiving the attachment portion 52. The attachment portion 52 and hole 64 are sized to enable the attachment portion 52 to slide in the hole 64 in order to align a center of mass of the PET detector 28 with the vertical axis 30. Thus, each PET detector 28 may be adjusted within its corresponding hole 64 as needed in order to accommodate the length of the PET detector 28 to ensure that the center of mass of each PET detector 28 is aligned with vertical axis 30. Upon alignment of the PET detector 28 with the vertical axis 30, a fastener may be used to affix the PET detector 28 in the aligned position. The attachment portion 52 and PET detector 28 may be formed as a one-piece configuration such that the attachment portion 52 and PET detector 28 are integrally or unistructurally formed. Alternatively, the attachment portion 52 and the PET detector 28 may be separate components wherein the attachment portion 52 is attached to the PET detector 28 with a fastener or adhesive. In another embodiment, the attachment portion 52 is instead formed in the backplane 24 and the hole 64 is formed in the PET detector 28.

Figure 7B:
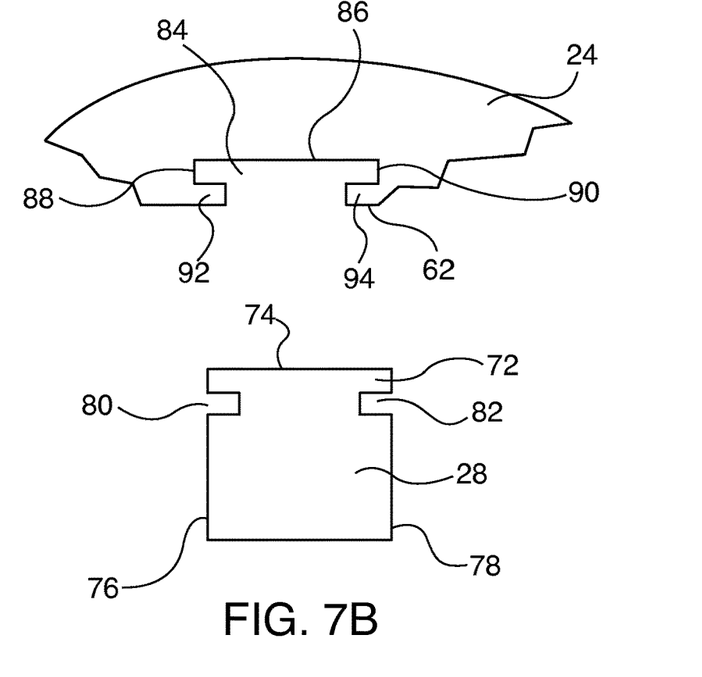
FIG. 7B is an alternate embodiment of the attachment portion.

Referring to FIG. 7B, an embodiment for an alternate attachment portion 72 is shown. In this embodiment, the PET detector 28 has a substantially rectangular shape and includes a horizontal top wall 74 located between substantially parallel sidewalls 76,78. The attachment portion 72 includes grooves 80,82 formed in the sidewalls 76,78, respectively, that extend along a length of the PET detector 28. The inner circumference 62 includes a substantially rectangular hole 84 defined by a horizontal top wall 86 located between parallel sidewalls 88,90 to form a substantially rectangular shape. Inwardly projecting portions 92,94 extend from the sidewalls 88,90, respectively, to form a shape that corresponds to the attachment portion 72. The projecting portions 92,94 are received by the grooves 80,82, respectively, to enable the attachment portion 72 to slide in the hole 84 in order to align a center of mass of the PET detector 28 with the vertical axis 30. Thus, each PET detector 28 may be adjusted within the hole 84 as needed in order to accommodate the length of the PET detector 28 to ensure that the center of mass is aligned with vertical axis 30. Upon alignment of the PET detector 28 with the vertical axis 30, a fastener may be used to affix the PET detector 28 in the aligned position. The attachment portion 72 and PET detector 28 may be formed as a one-piece configuration such that the attachment portion 72 and PET detector 28 are integrally or unistructurally formed. Alternatively, the attachment portion 72 and the PET detector 28 may be separate components wherein the attachment portion 72 is attached to the PET detector 28 with a fastener or adhesive. In another embodiment, the attachment portion 72 is instead formed in the backplane 24 and the hole 84 is formed in the PET detector 28. In still another embodiment, an indexing arrangement may be used wherein a plurality of threaded holes is formed along a length of a PET detector 28. A bracket hole of a bracket is then aligned with at least one threaded hole in order to locate the PET detector 28 in a desired position. A fastener is then inserted into the bracket hole and is threadably engaged with the aligned threaded hole to secure the PET detector 28.

Figure 8:
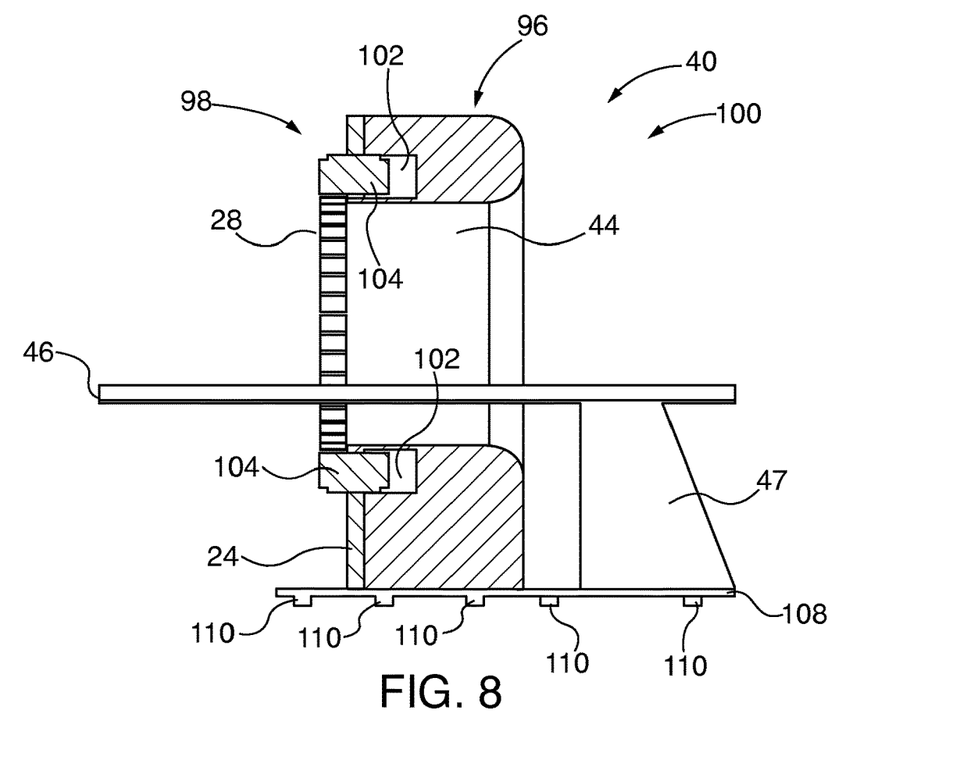
FIG. 8 is a partial cross sectional side view of a gantry of a combined system having in-line PET detectors wherein a portion of each PET detector is located in an annular cavity of a CT imaging system.
Figure 9:
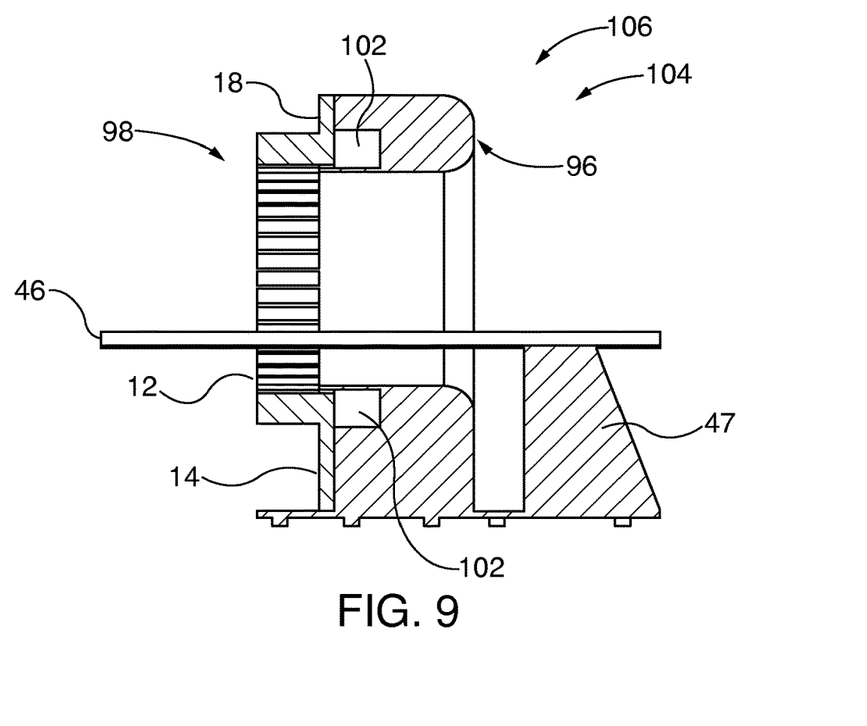
FIG. 9 is a partial cross sectional side view of a gantry of a conventional combined system having cantilevered PET detectors.

Referring to FIG. 8, a partial cross sectional side view of a gantry 100 of the combined system 40 is shown which depicts CT 96 and PET 98 portions of the combined system 40. Existing CT systems 96 include an annular cavity 102 positioned around the tunnel 44. In accordance with the invention, portions 104 of the in-line PET detectors 28 extending from the backplane 24 toward the CT system 96 are located within the annular cavity 102. Referring to FIG. 9, a partial cross sectional side view of a gantry 104 conventional combined CT and PET system 106 having the cantilevered PET detectors 12 is shown. As can be seen from FIG. 9, the cantilevered PET detectors 12 extend from the face 18 of the backplane 14 away from the CT system 96 and do not enter the annular cavity 102. Thus, the configuration of the present invention reduces a size of the gantry 100 as compared to the gantry 104 of conventional combined system 106 utilizing cantilevered PET detectors 12 that are not located in the annular cavity 102. This results in a reduced footprint for the gantry 100. Further, the current invention provides access to the in-line PET detectors 28 for servicing. In addition, reversing the cantilevered PET detectors 12 such that the cantilevered PET detectors 12 are located within the annular cavity 102 would not provide access to the cantilevered PET detectors 12 since access is blocked by the backplane 14.

In areas that are prone to earthquakes, such as in the state of California, regulations have been promulgated requiring that medical gantries (such as CT systems) must continue to operate normally after an earthquake. As previously described, it is desirable to combine CT and PET scanning techniques to provide a co-registered image or series of images to assist in non-invasively study physiological processes and structures within the body. Referring back to FIG. 8, the CT 96 and PET 98 portions of the combined system 40 along with the bed traversing mechanism 47 and bed 46 are each mounted to a common base element 108. Seismic isolation elements 110 are attached to the base element 108 to isolate the CT 96 and PET 98 portions, bed traversing mechanism 47 and bed 46 from a seismic event such as an earthquake. By way of example, the seismic isolation elements 110 may include known springs, dampers, ball bearings and other seismic isolation elements. By using seismic isolation elements 110, stresses generated on the CT 96 and PET 98 portions and bed traversing mechanism 47 are substantially reduced as compared to anchoring the CT 96 and PET 98 portions and bed traversing mechanism 47 to the floor.

Figure 10:
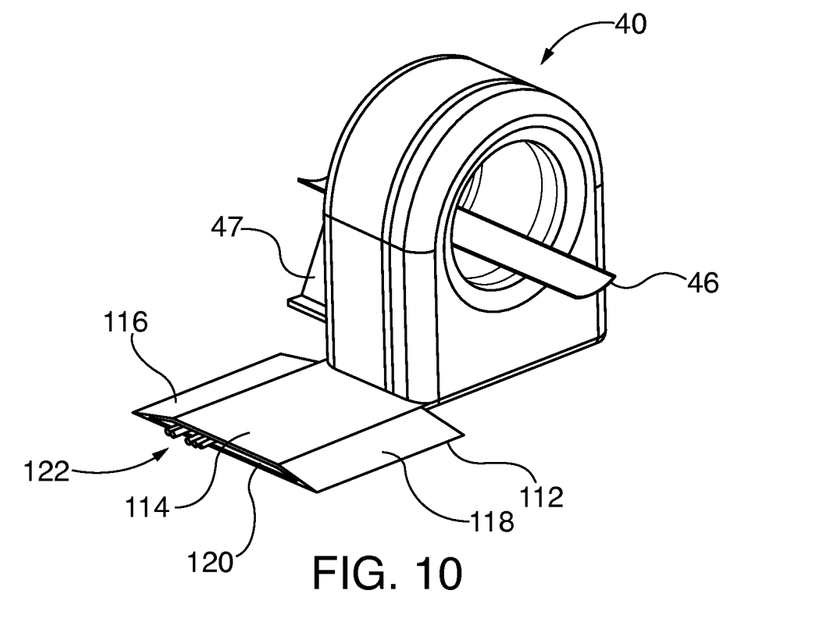
FIG. 10 shows a ramp for use in conjunction with the combined system.
Figure 11:
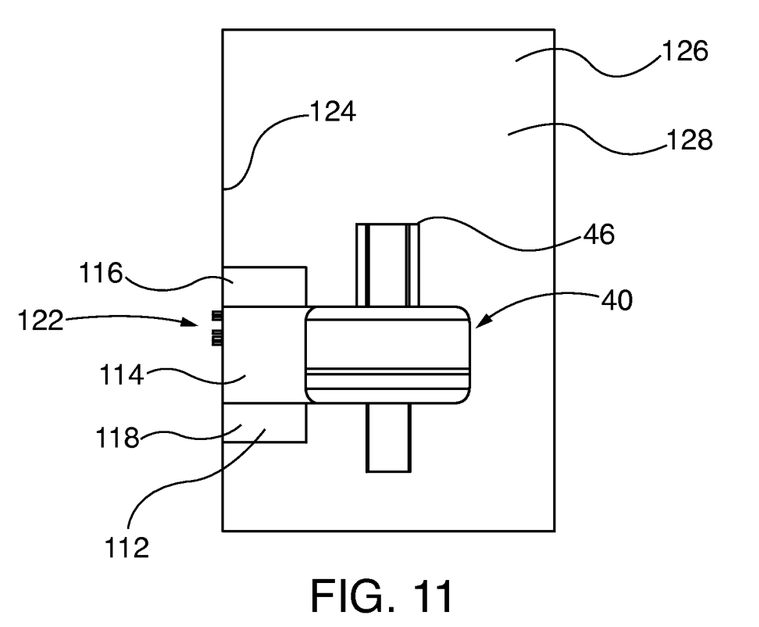
FIG. 11 is a top view of the ramp and combined system located in a scanner room.

Referring to FIGS. 10 and 11, a ramp 112 for use in conjunction with the combined system 40 is shown. The ramp 112 is attached to the combined system 40 and includes a horizontal section 114 located between ramp sections 116,118 to form a cavity 120. Electrical, data and water conduits 122 for the combined system are housed in the cavity 120. The ramp 112 is located against a wall 124 of a scanner room 126 and allows personnel, patients and equipment to transit without being obstructed by the conduits 122.

Additional length (i.e. slack) for the conduits 122 is also housed in the cavity 120. The slack accommodates movement of the combined system 40 as a result of a seismic event so that the conduits 122 are not damaged and normal operation of the combined system 40 is maintained after the seismic event. Further, the ramp 112 moves with the combined system 40 during the seismic event. The ramp 112 obviates the need for forming a trench in the scanner room floor 128 which is expensive.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A positron emission tomography (PET) detector configuration for a combined PET and computed tomography (CT) imaging system having a tunnel, comprising:

a backplane having a vertical axis that extends through a vertical plane in the backplane to form a vertical neutral backplane axis and a horizontal axis that extends through an aperture of the backplane;

a plurality of PET detectors located about the aperture, wherein each PET detector includes an attachment portion that attaches to the backplane to form a plurality of PET detectors arrangement wherein each PET detector arrangement extends through the backplane and wherein each PET detector arrangement has a detector axis oriented in the same plane as the vertical neutral backplane axis and a shape of each PET detector arrangement about the detector axis is symmetrical to define a detector axis of symmetry wherein a center of mass of each PET detector arrangement is located on the detector axis of symmetry and wherein the center of mass of each PET detector arrangement is in-line with the vertical neutral backplane axis.

2. The PET detector configuration according to claim 1, wherein the attachment portion is located on a horizontal surface of each PET detector for slidably attaching each PET detector to the backplane.

3. The PET detector configuration according to claim 2, wherein the attachment portion has a substantially dovetail shape.

4. The PET detector configuration according to claim 2, wherein the attachment portion has a substantially rectangular shape.

5. The PET detector configuration according to claim 1, wherein each PET detector is a time-of-flight (TOF) detector.

6. The PET detector configuration according to claim 1, wherein each PET detector includes photomultiplier tubes (PMTs).

7. The PET detector configuration according to claim 1, wherein each PET detector includes avalanche photo diodes (APDs).

8. The PET detector configuration according to claim 1, wherein each PET detector includes silicon photo multipliers (SiPMs).

9. A positron emission tomography (PET) detector configuration for a combined PET and computed tomography (CT) imaging system, wherein the CT system includes an annular cavity:

a backplane having a vertical axis that extends through a vertical plane in the backplane to form a vertical neutral backplane axis and a horizontal axis that extends through an aperture of the backplane;

a plurality of PET detectors located about the aperture, wherein each PET detector includes an attachment portion that attaches to the backplane to form a plurality of PET detectors arrangement wherein each PET detector arrangement extends through the backplane and wherein each PET detector arrangement has a detector axis oriented in the same plane as the vertical neutral backplane axis and a shape of each PET detector arrangement about the detector axis is symmetrical to define a detector axis of symmetry wherein a center of mass of each PET detector arrangement is located on the detector axis of symmetry and wherein the center of mass of each PET detector arrangement is in-line with the vertical neutral backplane axis to reduce a strength needed for structural integrity of the backplane relative to a cantilevered detector arrangement.

10. The PET detector configuration according to claim 9, wherein the attachment portion is located on a horizontal surface of each PET detector for slidably attaching each PET detector to the backplane.

11. The PET detector configuration according to claim 10, wherein the attachment portion has a substantially dovetail shape.

12. The PET detector configuration according to claim 10, wherein the attachment portion has a substantially rectangular shape.

13. The PET detector configuration according to claim 9, wherein each PET detector is a time-of-flight (TOF) detector.

14. The PET detector configuration according to claim 9, wherein each PET detector includes photomultiplier tubes (PMTs).

15. The PET detector configuration according to claim 9, wherein each PET detector includes avalanche photo diodes (APDs).

16. The PET detector configuration according to claim 9, wherein each PET detector includes silicon photo multipliers (SiPMs).

17. A combined positron emission tomography (PET) and computed tomography (CT) imaging system, comprising:

a CT imaging section;

a PET imaging section including a plurality of PET detectors wherein each PET detector includes an attachment portion that attaches to the backplane to form a plurality of PET detectors arrangement wherein each PET detector arrangement extends through the backplane and has a detector axis oriented in the same plane as a vertical neutral backplane axis wherein a shape of each PET detector arrangement about the detector axis is symmetrical to define a detector axis of symmetry wherein a center of mass of each PET detector arrangement is located on the detector axis of symmetry, the PET imaging section further including a backplane having a vertical axis that extends through a vertical plane in the backplane to form the vertical neutral backplane axis and a horizontal axis that extends through an aperture of the backplane and wherein the center of mass of each PET detector arrangement is located in-line with the vertical neutral backplane axis of the backplane;

a bed traversing mechanism for holding a patient;

a base element, wherein the CT and PET imaging sections and the bed traversing mechanism are mounted to the base element; and at least one seismic isolation element mounted to the base element for isolating the CT and PET imaging sections and the bed traversing mechanism from a seismic event.

18. A combined positron emission tomography (PET) and computed tomography (CT) imaging system, comprising:

a CT imaging section;

a PET imaging section including a plurality of PET detectors wherein each PET detector includes an attachment portion that attaches to the backplane to form a plurality of PET detectors arrangement wherein each PET detector arrangement extends through the backplane and has a detector axis oriented in the same plane as a vertical neutral backplane axis wherein a shape of each PET detector arrangement about the detector axis is symmetrical to define a detector axis of symmetry wherein a center of mass of each PET detector arrangement is located on the detector axis of symmetry, the PET imaging section further including a backplane having a vertical axis that extends through a vertical plane in the backplane to form the vertical neutral backplane axis and a horizontal axis that extends through an aperture of the backplane and wherein the center of mass of each PET detector arrangement is located in-line with the vertical neutral backplane axis of the backplane;

a bed traversing mechanism for holding a patient; and a ramp having a cavity for housing conduits attached to the combined imaging system, wherein the ramp is attached to the combined imaging system and moves with the combined imaging system during a seismic event.

\* \* \* \* \*